United States Patent [19]

Giraudon et al.

[11] Patent Number: 4,622,323

[45] Date of Patent: Nov. 11, 1986

[54] FUNGICIDAL 2-CYANOBENZIMIDAZOLE DERIVATIVES

[75] Inventors: Raymond Giraudon, Lesigny; Georges Santini, Lyons, both of France

[73] Assignee: Rhone-Poulenc Agrochimie, Lyons, France

[21] Appl. No.: 698,846

[22] Filed: Feb. 6, 1985

[30] Foreign Application Priority Data

Feb. 6, 1984 [FR] France .............................. 84 02118

[51] Int. Cl.$^4$ ..................... A01N 43/52; A01N 43/84; C07D 413/12; C07D 235/24
[52] U.S. Cl. ................................... 514/228; 514/229; 514/395; 544/139; 548/327; 548/329
[58] Field of Search ................ 548/329, 327; 544/139; 514/395, 228, 229

[56] References Cited

U.S. PATENT DOCUMENTS

| | | | |
|---|---|---|---|
| 3,576,818 | 4/1971 | Samuel et al. | 548/331 |
| 4,109,004 | 8/1978 | Percival | 548/329 X |
| 4,536,502 | 8/1985 | Giraudon et al. | 514/227 |

*Primary Examiner*—Richard A. Schwartz
*Attorney, Agent, or Firm*—Burns, Doane, Swecker & Mathis

[57] ABSTRACT

The invention relates to new 2-cyanobenzimidazole derivatives.

These compounds have the formula (II):

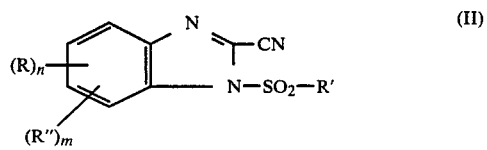

with:
- n 0, 1 or 2,
- m 1 or 2,
- R halogen; lower alkyl or lower alkoxy or lower alkylthio, optionally halogenated; $NO_2$—, CN—,
- R' lower alkyl or lower cycloalkyl, optionally halogenated, amino optionally substituted with one or two alkyl radicals, or a nitrogen atom substituted with two radicals forming with this nitrogen atom a heterocycle which contains from 4 to 6 members and from 1 to 3 hetero atoms in the ring,
- R'' optionally substituted phenoxy or optionally substituted phenylthio.

They can be used in agriculture, especially for controlling phytopathogenic fungi.

7 Claims, No Drawings

FUNGICIDAL 2-CYANOBENZIMIDAZOLE DERIVATIVES

The present patent application relates to new 2-cyanobenzimidazole derivatives, and also to the preparation of these compounds. In addition, it relates to the pesticidal compositions, especially anti-fungal compositions, which can be used in agriculture and which contain, as active substance, one of these compounds, and also to the pesticidal treatments, and, more especially, the anti-fungal treatments performed by means of these compounds. It relates finally to several chemical compounds which can be used for preparing the compounds according to the invention.

The new 2-cyanobenzimidazole derivatives according to the invention are of the general formula (II):

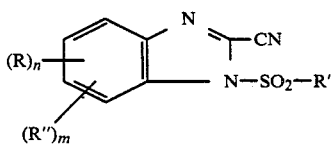
(II)

in which n, m, R, R' and R" have the significance given below, it being understood that, in that which follows, except where otherwise stated, the adjective "lower" applied to an organic radical means that this radical contains at most 6 carbon atoms.

In the formula (II):
n denotes an integer which can equal 0, 1 or 2
m denotes an integer equal to 1 or 2
R denotes a halogen atom or a lower alkyl radical optionally substituted with one or more halogen atoms; a lower alkoxy radical optionally substituted with one or more halogen atoms; a lower alkylthio radical optionally substituted with one or more halogen atoms; nitro; cyano, it being understood that, when n equals 2, the substituents R can be either identical or different,
R' denotes a lower alkyl or lower cycloalkyl radical optionally substituted with one or more halogen atoms (e.g., methyl, ethyl, isopropyl, trichloromethyl, trifluoromethyl radicals, and the like); or an amino radical optionally substituted with one or two lower alkyl radicals, which may be identical or different, and are themselves optionally substituted (e.g. with one or more halogen atoms); or a nitrogen atom substituted with two radicals forming with this nitrogen atom a heterocycle, which is itself optionally substituted by, for example, one or more substituents such as halogen atoms and lower alkoxy and lower alkylthio radicals and which contains from 4 to 6 members and from 1 to 3 hetero atoms in the ring (e.g., a morpholino radical, pyrrolidino radical, and the like).
R" denotes an optionally substituted phenoxy, radical or an optionally substituted phenylthio radical, it being understood that when m equals 2, the substituents R" can be either identical or different.

Advantageously, the substituent or substituents of the phenoxy and/or phenylthio radicals can be chosen from the halogen atoms, preferably fluorine, chlorine or bromine, and the lower alkyl, cyano, nitro, lower alkoxy and lower haloalkyl radicals, e.g., the trifluoromethyl radical.

Among the compounds of formula (II), a subfamily which is preferred on account of its outstanding antifungal properties consists of the compounds for which:
n equals 0 or 1 (preferably n equals 0),
m equals 1
R denotes a halogen atom or a cyano, nitro, trifluoromethyl, trifluoromethoxy or trifluoromethylthio radical,
R' denotes a ($C_2$-$C_4$) dialkylamino radical or ($C_1$-$C_3$) alkyl radical, optionally halogenated (R' preferably denotes a dimethylamino radical),
R" denotes a phenoxy radical substituted with one to three substituents chosen from the halogen atoms and the trifluoromethyl radical.

The invention relates, in addition, to a process for preparing the compounds according to the formula (II).

This process consists in reacting a 2-cyanobenzimidazole of formula (III)

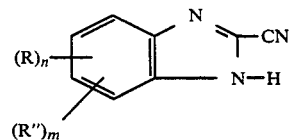
(III)

in which R, R", m and n have the same significance as in the formula (II), or a salt, (preferably an alkali metal or ammonium salt) of this 2-cyanobenzimidazole (III), with a halide of formula (IV)

$$X-SO_2R'$$ (IV)

in which R' has the same significance as in the formula (II) and X denotes a halogen atom, preferably a chlorine atom.

The reaction of the 2-cyanobenzimidazole (III) with the halide (IV) is advantageously performed in the presence of an acceptor for acid, in anhydrous or non-anhydrous medium, in a solvent which is inert under the conditions of the reaction, generally at the boiling point of the solvent. As acceptors for acid, there may be mentioned inorganic bases, e.g. caustic soda or caustic potash, alkali metal carbonates or alkaline earth metal carbonates, and nitrogenous bases such as triethylamine. As solvents, polar aprotic solvents are advantageously used, e.g. dimethylformamide, dimethylacetamide, dimethyl sulphoxide, acetone, methyl ethyl ketone, acetonitrile, and N-methylpyrrolidone. If desired, this reaction can be performed in the presence of a suitable catalyst. As a suitable catalyst, there may be mentioned phase transfer catalysts, e.g. quaternary ammonium derivatives.

The reaction of the salt (alkali metal or ammonium salts) of the 2-cyanobenzimidazole (III) with the halide (IV) does not require the presence of an acceptor for acid. It is performed in anhydrous or non-anhydrous medium, in a solvent which is inert under the conditions of the reaction, generally at the boiling point of the solvent. The polar aprotic solvents mentioned above can be advantageously used in this reaction.

If desired, this reaction can be performed in the presence of a suitable catalyst, e.g. a phase transfer catalyst (e.g. a quaternary ammonium derivative).

The alkali metal salt or ammonium salt of the compound (III) is prepared in a prior operation, optionally performed in situ, by the action of a suitable base (for example caustic soda, caustic potash or ammonia) or an alkali metal carbonate or an alkali metal alcoholate (e.g. sodium methylate, sodium ethylate or potassium ethylate) on this compound (III).

At the end of the reaction, whichever procedure is used, the compound formed is isolated from the reaction medium by any method known per se, e.g. by distillation of the solvent or by crystallisation of the product in the reaction medium, or by filtration, and if necessary this compound is then purified by customary methods, such as recrystallisation in a suitable solvent.

The 2-cyanobenzimidazole of the formula (III) which serves as starting substance, can be prepared, as described below, by the action of ammonia on a 2-(trihalomethyl)benzimidazole of formula (V)

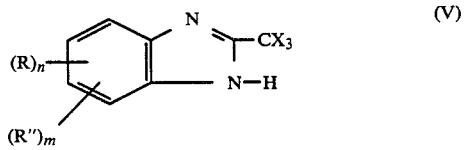

in which R, R'', m and n have the same significance as in the formula (II) and X denotes a halogen atom, preferably chlorine, working according to the method described in European patent application No. 0,087,375 (Method A) and U.S. Pat. No. 3,576,818.

It can also be prepared according to one or other of the Methods B and C described in European patent application No. 0,087,375.

The compound of formula (V) can be prepared by the action of methyl trichloroacetimidate on the 1,2-diaminobenzene of formula (VI)

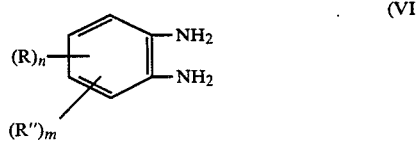

in which R, R'', m and n have the same significance as in the formula (V), or on a salt of this compound formed with a strong acid.

The reaction is advantageously performed starting at room temperature, in acetic acid medium, or in lower alkanols such as ethanol or methanol. It can also be performed at the refluxing temperature of the solvents used. If desired, the conversion of the 1,2-diaminobenzene of formula (VI) to the 2-cyanobenzimidazole (III) can be accomplished by performing the two stages described above successively without isolating the intermediate 2-(trihalomethyl)benzimidazole of formula (V) formed.

The 1,2-diaminobenzene of formula (VI) can be prepared from the nitroaniline of formula (VII)

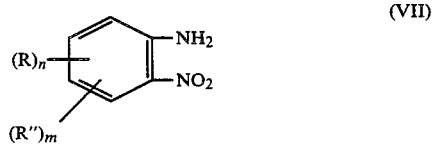

in which R, R'', m and n have the same significance as in formula (V), by reduction of the nitro group to an amino group. This reduction can be accomplished by any means known per se for reducing a nitrobenzene to an aniline without affecting the other substituents present on the benzene ring, e.g. by the action of stannous chloride in the presence of concentrated hydrochloric acid.

The nitroaniline (VII) can be obtained by the action of sulphuric acid on the corresponding N-(nitrophenyl)acetamide.

The compounds of formulae (III), (V), (VI) and (VII) are included within the scope of the present invention as new products which can be used for carrying out the preparation process described above.

The examples below, which are described without implied limitation, illustrate the preparation of the compounds according to the invention and their use as fungicides. The structures of the compounds described in these examples were confirmed by nuclear magnetic resonance (NMR) spectrometry and/or infrared spectrometry.

EXAMPLE 1

Preparation of
2-cyano-5-[2-chloro-4-(trifluoromethyl)phenoxy]-1-(dimethylsulphamoyl)benzimidazole (compound 1A)
mixed with
2-cyano-6-[2-chloro-4-(trifluoromethyl)phenoxy]-1-(dimethylsulphamoyl)benzimidazole (compound 1B)

To a suspension of caustic potash flakes (1.04 g; 16.2 millimoles) in acetone (60 ml), 2-cyano-5-[2-chloro-4-(trifluoromethyl)phenoxy]benzimidazole (5.5 g; 16.2 millimole) is added at room temperature (approximately 20° C.). Complete dissolution of the reagents is observed, and a rise in temperature which reaches 35° C.

To the reaction mixture, dimethylsulphamoyl chloride (1.75 ml; 16.2 millimoles) is then added in the course of 10 minutes, and the reaction mixture is stirred for 18 hours, and then concentrated. An oil is obtained which is chromatographed on silica (200 g) with methylene chloride as eluent.

The desired compound (4.2 g) is thus obtained in the form of an oil which crystallises after 1 week. M.p. 90° C. Yield 58.3%.

2-Cyano-5-[2-chloro-4-(trifluoromethyl)phenoxy]-benzimidazole was prepared from 4-[2-chloro-4-(trifluoromethyl)phenoxy]-1,2-diaminobenzene as described below:

To a solution of 4-[2-chloro-4-(trifluoromethyl)-phenoxy]-1,2-diaminobenzene (35 g; 0.122 mole) in acetic acid (165 ml), methyl trichloroacetimidate (15.1 ml; 0.122 mole) is added. After 15 minutes, a rise in temperature to 52° C. is observed. The mixture is then left to cool at 25° C. by maintaining it with stirring for 18 hours.

The solution thus obtained is then run dropwise into 84% strength ammonia solution (2 liters in the course of 20 minutes at a temperature between 10° and 15° C. The reaction mixture is maintained with stirring at 25° C. for 3 hours, and then filtered. The solid obtained is chromatographed on a silica column with an 80:20 mixture of toluene and ethyl acetate as eluent. 2-Cyano-5-[2-chloro-4-(trifluoromethyl)phenoxy]benzimidazole (6.8 g) is obtained, m.p. 192° C. Yield 16.4%.

4-[2-Chloro-4-(trifluoromethyl)phenoxy]-1,2-diaminobenzene was prepared as described below:

1-Amino-2-nitro-5-[2-chloro-4-(trifluoromethyl-phenoxy]benzene (44 g; 0.138 mole) is added in small portions to a solution of stannous chloride dihydrate (117.5 g; 0.52 mole) in concentrated hydrochloric acid (density 1.19) (600 ml). The addition which is performed in the course of 15 minutes causes a rise in temperature from 20° to 45° C.

The reaction mixture is then shaken for 2 hours at 25° C. After distilled water (one liter) and methylene chloride (one liter) are added, the mixture is made alkaline up to pH 13 by means of concentrated caustic soda, with cooling so that the temperature does not exceed 25° C. After decantation, the aqueous phase is again extracted with methylene chloride (2×400 ml). The combined organic phases are dried over sodium sulphate and then concentrated under vacuum to give 1,2-diamino-4-[2-chloro-4-(trifluoromethyl)phenoxy]-benzene (35 g; yield 88.5%) in the form of a brown oil.

1-Amino-2-nitro-5-[2-chloro-4-(trifluoromethyl)-phenoxy]benzene was prepared as described below:

To concentrated sulphuric acid (350 ml), N-[2-nitro-5(2-chloro-4-{trifluoromethyl}phenoxy)phenyl]acetamide (75.5 g; 0.2 mole) is added in small portions in the course of twenty minutes. The temperature rises to 30° C. The reaction mixture is then heated to 50° C. for 2 hours and, after being cooled, is then poured onto ice/water (1 kg). The solid thus obtained is purified by chromatography to give 1-amino-2-nitro-5-[2-chloro-4-(trifluoromethyl)phenoxy]benzene (44 g), m.p. 100° C. Yield 69%.

EXAMPLE 2

Working according to the method described in the above example, the compounds or mixtures of compounds below were prepared:

2A+2B: 50:50 mixture of 2-cyano-1-dimethylsulphamoyl-5-(phenylthio)benzimidazole and 2-cyano-1-dimethylsulphamoyl-6-(phenylthio)benzimidazole. M.p. 100° C.

3A+3B: 93:7 or 7:93 mixture of 2-cyano-1-dimethylsulphamoyl-6-(phenoxy)benzimidazole and 2-cyano-1-dimethylsulphamoyl-5-(phenoxy)benzimidazole. M.p. 170° C.

4A+4B: 66:34 or 34:66 mixture of 2-cyano-1-dimethylsulphamoyl-6-phenoxy-5-(trifluoromethyl)benzimidazole and 2-cyano-1-dimethylsulphamoyl-5-phenoxy-6-(trifluoromethyl)benzimidazole. M.p.: 138° C. Yield 69.4%.

5A+5B: 60:40 or 40:60 mixture of 2-cyano-1-dimethylsulphamoyl-6-(2,4-dichlorophenoxy)-5-(trifluoromethyl)benzimidazole and 2-cyano-1-dimethylsulphamoyl-5-(2,4-dichlorophenoxy)-6-(trifluoromethyl)benzimidazole, m.p. 115°–125° C. Yield 81%.

The formulae of these compounds are shown in Table I at the end of the description.

EXAMPLE 3

Greenhouse test on tomato blight

Tomato plants (*Lycopersicum esculentum*), of Marmande variety, are cultivated in pots. When these plants are one month old (5 to 6 leaf stage, height 12 to 15 cm), they are treated by spraying them with an aqueous solution or suspension of the substance to be tested, at the desired concentration and containing 0.02% of a condensate of sorbitan monooleate and 20 molecules of ethylene oxide. Each tomato plant receives approximately 5 ml of the solution or dispersion. For each concentration of active substance to be tested, the treatment is performed on eight plants. Plants used as controls are treated with a solution which does not contain active substance, but which contains 0.02% of the same condensate of sorbitan monooleate and ethylene oxide.

After 4 hours of drying, each plant is contaminated by spraying it with an aqueous suspension of spores of *Phytophthora infestans,* which is responsible for tomato blight, in the proportion of approximately 1 ml/plant (equivalent to approximately $2 \times 10^5$ spores per plant).

After this contamination, the tomato plants are incubated for two to three days at approximately 17° C. in an atmosphere saturated with moisture, and then for four days at approximately 22° C. and 70% to 80% relative humidity.

Seven days after the contamination, comparison is made between the results obtained in the case of the plants treated with the active substance to be tested and those obtained in the case of the plants used as controls, and the minimal inhibitory concentration which causes from 95 to 100% inhibition of the development of the fungus in question (MIC 95-100) is determined.

Under these conditions, it is observed that, for the compounds or mixtures of compounds described in the above examples, this concentration was respectively as follows:

| Compound or mixture tested | MIC (95–100) *Phytophthora infestans* in mg/l |
|---|---|
| 1A + 1B | less than 125 |
| 2A + 2B | greater than 500 |
| 3A + 3B | greater than 500 |
| 4A + 4B | less than 500 |
| 5A + 5B | less than 125 |

EXAMPLE 4

Greenhouse test on the blue mould of tobacco

The procedure is as in the example above, except that the plants are tobacco plants (*Nicotiana tabacum*) of Samson variety and that these plants are contaminated by spores of *Peronospora tabacina,* which is responsible for blue mould of tobacco.

Under these conditions, it was observed that, for the compounds or mixtures of compounds described in the above examples, the minimal inhibitory concentrations which cause from 95 to 100% inhibition of the fungus in question (MIC 95-100) are respectively as follows:

| Compounds or mixture tested | MIC (95–100) *Peronospora tabacina* in mg/l |
|---|---|
| 1A + 1B | less than 8 |
| 2A + 2B | greater than 500 |
| 3A + 3B | greater than 500 |
| 4A + 4B | greater than 500 |
| 5A + 5B | 500 |

The compounds according to the invention are advantageously used as anti-fungal compounds in the field of agriculture. They possess contact action and systemic action, and can preferably be used preventively, but also curatively, for controlling various phytopathogenic fungi, e.g. many phycomycetes and basidiomycetes, especially *Phytophthora infestans* (potato blight, tobacco blight, tomato blight) and *Plasmopara viticola* (downy mildew of vine). Some of these compounds can also be advantageously used as mite-killers, especially in respect of plant-eating mites.

For their use in practice, the compounds according to the invention are generally not employed alone. Most frequently, they are employed in compositions which generally comprise, in addition to the active substance, an inert support (or diluent) and/or a surfactant which are compatible with the active substance.

These compositions also form part of the present invention. They usually contain from 0.001 to 95% by weight of active substance. Their surfactant content is generally between 0% and 20% by weight.

The term "support", in the present account, denotes an organic or inorganic material, either natural or synthetic, with which the active substance is mixed to facilitate its application to the plant, seeds or the soil. This support is hence generally inert and must be acceptable for agricultural purposes, especially acceptable to the treated plant. The support can be solid (clays, natural or synthetic silicates, silica, chalks, resins, waxes, solid fertilisers and the like) or liquid (water, alcohols, ketones, petroleum fractions, aromatic or paraffinic hydrocarbons, chlorinated hydrocarbons, liquefied gas, and the like).

The surfactant can be an emulsifying agent, dispersant or wetting agent of the ionic or nonionic type. There may be mentioned, e.g., salts of polyacrylic acids; salts of lignosulphonic, phenolsulphonic or naphthalenesulphonic acids; polycondensates of ethylene oxide with fatty alcohols, with fatty acids, with fatty amines or with substituted phenols (especially alkylphenols, arylphenols or styrylphenol); salts of sulphosuccinic acid esters; taurine derivatives (especially alkyltaurates); and phosphoric esters of polycondensates of ethylene oxide with alcohols or phenols. The presence of at least one surfactant is generally essential, above all when the inert support is insoluble in water and the vector agent for the application is water.

Compositions used in the invention can take quite diverse forms, solid or liquid.

As solid forms of compositions, there may be mentioned powders for dusting (having a content of active substances which can range up to 100%).

As liquid forms of compositions, or forms designed to make liquid compositions when applied, there may be mentioned solutions, in particular water-soluble concentrates, emulsifiable concentrates, emulsions, flowables, aerosols, wettable powders (or powder for spraying), pellets and pastes.

The emulsifiable or soluble concentrates most frequently include 10 to 80% of active substance, whereas the ready-to-apply emulsions or solutions contain 0.001 to 20% of active substance. In addition to the active substance and the solvent, the emulsifiable concentrates can contain, where necessary, a suitable co-solvent and suitable additives (from 2 to 20%), e.g. stabilisers, surfactants, especially of the emulsive type, penetrants, corrosion inhibitors, colourings and adhesives.

From these concentrates, by dilution with water, there can be obtained emulsions of any desired concentration, which are especially suitable for application to crops.

The flowables, which can also be applied by spraying, are prepared so as to obtain a stable fluid product which does not settle out, and they usually contain active substance (from 10 to 75%), surfactants (0.5 to 15%), thixotropic agents (from 0.1 to 10%), suitable additives (from 0 to 10%), e.g. antifoams, corrosion inhibitors, stabilisers, penetrants and adhesives and, as support, water or an organic liquid in which the active substance is only slightly soluble or insoluble; certain organic solid materials or inorganic salts can be dissolved in the support to assist in preventing sedimentation, or as anti-freeze for the water.

By way of example, there follows the composition of several aqueous suspensions according to the invention:

EXAMPLE A

An aqueous suspension is prepared containing:

| | |
|---|---|
| active substance (compound No. 1A + 1B) | 500 g/l |
| wetting agent (polycondensate of ethylene oxide with $C_{13}$ synthetic alcohol) | 10 g/l |
| dispersant (salified phosphate of polyaryl phenol condensed with ethylene oxide) | 50 g/l |
| anti-freeze (propylene glycol) | 100 g/l |
| thickener (polysaccharide) | 1.6 g/l |
| biocide (sodium 4-[methylhydroxy]benzoate) | 3.3 g/l |
| water | q.s. 1 liter. |

A cream-coloured fluid flowable is thereby obtained.

EXAMPLE B

Aqueous suspension

An aqueous suspension is prepared containing:

| | |
|---|---|
| active substance (compound No. 1A + 1B) | 100 g/l |
| wetting agent (polycondensate of ethylene oxide with alkylphenol) | 5 g/l |
| dispersant (sodium naphthalenesulphonate) | 10 g/l |
| anti-freeze (propylene glycol) | 100 g/l |
| thickener (polysaccharide) | 3 g/l |
| biocide (formaldehyde) | 1 g/l |
| water | q.s. 1 liter. |

EXAMPLE C

Aqueous suspension

An aqueous suspension is prepared containing:

| | |
|---|---|
| active substance (compound No. 1A + 1B) | 250 g/l |
| wetting agent (polycondensate of ethylene oxide with $C_{13}$ synthetic alcohol) | 10 g/l |
| dispersant (sodium lignosulphonate) | 15 g/l |
| anti-freeze (urea) | 50 g/l |
| thickener (polysaccharide) | 2.5 g/l |
| biocide (formaldehyde) | 1 g/l |
| water | q.s. 1 liter. |

The wettable powders (or powders for spraying) are usually prepared so as to contain 20 to 95% of active substance, and they usually contain, in addition to the solid support, a wetting agent (from 0 to 5%), a dispersant (from 3 to 10%) and, where necessary, one or more stabilisers and/or other additives (from 0 to 10%), e.g. penetrants, adhesives or anticaking agents, colourings and the like.

By way of example, there follows the composition of several wettable powders.

EXAMPLE D

50% strength wettable powder

| | |
|---|---|
| active substance (compound No. 1A + 1B) | 50% |
| condensate of ethylene oxide with fatty alcohol (wetting agent) | 2.5% |
| condensate of ethylene oxide with styrylphenol (dispersant) | 5% |

-continued

| | |
|---|---|
| chalk (inert support) | 42.5% |

EXAMPLE E

10% strength wettable powder

| | |
|---|---|
| active substance (compound No. 1A + 1B) | 10% |
| branched type $C_{13}$ synthetic oxo alcohol, condensed with 8 to 10 molar equivalents of ethylene oxide (wetting agent) | 0.75% |
| neutral calcium lignosulphonate (dispersant) | 12% |
| calcium carbonate (inert filler) | q.s. 100% |

EXAMPLE F

75% strength wettable powder

Containing the same ingredients as in the preceding example, in the following proportions:

| | |
|---|---|
| active substance | 75% |
| wetting agent | 1.50% |
| dispersant | 8% |
| calcium carbonate (inert filler) | q.s. 100% |

EXAMPLE G

90% strength wettable powder

| | |
|---|---|
| active substance (compound No. 1 according to the invention) | 90% |
| condensate of ethylene oxide with fatty alcohol (wetting agent) | 4% |
| condensate of ethylene oxide with styrylphenol (dispersant) | 6% |

EXAMPLE H

50% strength wettable powder

| | |
|---|---|
| active substance (compound No. 1 according to the invention) | 50% |
| mixture of anionic and nonionic surfactants (wetting agent) | 2.5% |
| neutral sodium lignosulphonate (dispersant) | 5% |
| kaolin clay (inert support) | 42.5% |

To obtain these powders for spraying or wettable powders, the active substance is intimately mixed in suitable mixers with the additional substances, and the mixture is ground with mills or other suitable grinders. By this means, powders for spraying are obtained, the wettability and suspendibility of which are advantageous; they can be suspended in water at any desired concentration and this suspension can be used very advantageously, especially for application to plant leaves.

The compounds according to the invention are advantageously formulated in the form of pellets which can be dispersed in water, and are also included within the scope of the invention.

These dispersible pellets, of apparent density generally between approximately 0.3 and 0.6, are generally of particle size between approximately 150 and 2000 microns, and preferably between 300 and 1500 microns.

The content of active substance (compound No. 1A+1B) of these pellets is generally between approximately 1% and 90%, and preferably between 25% and 90%.

The remainder of the pellet is mainly composed of a solid filler, and optionally of surfactant adjuvants which endow the pellet with properties of dispersibility in water. These pellets can be of essentially two distinct types, according to whether or not the filler included is soluble in water. When the filler is water-soluble, it can be inorganic and is preferably organic. Excellent results have been obtained with urea. In the case of an insoluble filler, this is preferably inorganic, e.g. kaolin or bentonite. The filler is then accompanied by surfactants (in the proportion of 2 to 20% by weight of the pellet), of which surfactant adjuvants more than one half consists of at least one essentially anionic dispersant, such as an alkali metal polynaphthalenesulfonate or alkaline earth metal polynaphthalenesulphonate or an alkali metal lignosulphonate or alkaline earth metal lignosulphonate, the remainder consisting of nonionic or anionic wetting agents such as an alkali metal alkylnaphthalenesulphonate or alkaline earth metal alkylnaphthalenesulphonate.

Furthermore, although this is not essential, other adjuvants such as antifoaming agents can be added.

The pellet according to the invention can be prepared by mixing the necessary ingredients followed by granulation according to several techniques known per se (bowl granulator, fluidised bed, atomiser, extrusion and the like). The preparation is generally completed by crushing followed by sieving to the particle size chosen within the abovementioned limits.

The pellet is preferably obtained by extrusion, using the procedure described in the examples below.

EXAMPLE I

Dispersible granules containing 90% of active substance

In a mixer, the active substance (compound No. 1) (90% by weight) is mixed with urea beads (10%). The mixture is then ground in a toothed roll crusher. A powder is obtained which is moistened with approximately 8% by weight of water. The moist powder is extruded in a perforated roll extruder. A pellet is obtained which is dried, and then crushed and sieved so as to retain, respectively, only the pellets of size between 150 and 2000 microns.

EXAMPLE J

Dispersible pellets containing 75% of active substance

In a mixer, the following constituents are mixed:

| | |
|---|---|
| active substance (compound No. 1) | 75% |
| wetting agent (sodium alkylnaphthalenesulphonate) | 2% |
| dispersant (sodium polynaphthalenesulphonate) | 8% |
| water-insoluble inert filler (kaolin) | 15% |

This mixture is granulated in a fluidised bed in the presence of water, and then is dried, crushed and sieved so as to obtain pellets of size between 0.16 and 0.40 mm.

These pellets can be used alone, dissolved or dispersed in water so as to obtain the dose sought. They can also be used for preparing mixtures with other active substances, especially fungicides, the latter being in the form of wettable powders, pellets or aqueous suspensions.

As already stated, the aqueous dispersions and emulsions, for example of the compositions obtained by diluting with water a wettable powder or an emulsifiable concentrate according to the invention, are included within the general scope of the compositions which can be used in the present invention. The emulsions can be of the water-in-oil type or oil-in-water type and they can have a thick consistency like that of "mayonnaise".

The invention also relates to a process for treating plants against phytopathogenic fungi.

This process consists in applying to these plants an effective quantity of a composition containing, as active substance, a compound according to the formula (II). By "effective quantity", there is understood a quantity sufficient to enable the fungi present on these plants to be controlled and destroyed. The doses for use can, however, vary within wide limits according to the fungus to be combated, the type of crop, the climatic conditions and the compound used.

In practice, doses ranging from 5 g/hl to 100 g/hl, which substantially corresponds to doses of active substance per hectare of approximately 50 g/ha to 1000 g/ha, generally give good results.

TABLE I

| COMPOUND NO. | FORMULA | M.p. |
|---|---|---|
| 1A | | 192° C. |
| 1B | | |
| 2A | | Mixture of 2A + 2B (50:50): |
| 2B | | 100° C. |
| 3A | | 94° C. |
| 3B | | 170° C. |
| 4A | | Mixture of 4A + 4B (66:34 or 34:66): |

TABLE I-continued

| COMPOUND NO. | FORMULA | M.p. |
|---|---|---|
| | | 138° C. |
| 5A | | Mixture of 5A + 5B (60:40 or 40:60): |
| 5B | | 115–125° C. |

We claim:

1. A 2-cyanobenzimidazole derivative of the formula:

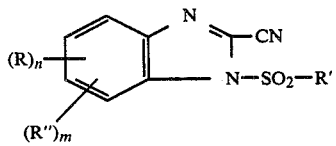

in which:
n denotes an integer equal to 0, 1 or 2,
m denotes an integer equal to 1 or 2,
R denotes a halogen atom or a lower alkyl radical optionally substituted with one or more halogen atoms; a lower alkoxy radical optionally substituted with one or more halogen atoms; a lower alkylthio radical optionally substituted with one or more halogen atoms; nitro; cyano, it being understood that, when n equals 2, the subsituents R can be either identical or different;
R' denotes a lower alkyl or lower cycloalkyl radical optionally substituted with one or more halogen atoms; or an amino radical optionally substituted with one or two lower alkyl radicals, which may be identical or different, and are themselves optionally substituted by one or more halogen atoms; or a nitrogen atom substituted with two radicals forming with this nitrogen atom a morpholino or pyrrolidino group;
R" denotes an optionally substituted phenoxy radical or an optionally substituted phenylthio radical the substituents in each instance being halogen, lower alkyl, cyano, nitro, lower alkoxy or lower haloalkyl.

2. A compound according to claim 1, in which:
n equals 0 or 1,
m equals 1
R denotes a halogen atom or a cyano, nitro, trifluoromethyl, trifluoromethoxy or trifluoromethylthio radical,
R' denotes a (C₂-C₄) dialkylamino radical or (C₁-C₃) alkyl radical, optionally halogenated, R" denotes a phenoxy radical substituted with one to three substituents chosen from the halogen atoms and the trifluoromethyl radical.

3. A compound according to claim 2, in which:
n equals 0,
m equals 1,
R' denotes a dimethylamino radical, and
R" denotes a phenoxy radical substituted with one to two substituents chosen from the halogen atoms and the trifluoromethyl radical.

4. A composition for agricultural use, which contains (i) as active substance a compound according to one of claims 1 to 3 in an amount effective to control phytopathogenic fungi and (ii) a carrier.

5. A composition according to claim 4, which contains, in addition to the active substance, a surfactant which is usable in agriculture.

6. A composition according to claim 5, which contains active substance (from 0.001 to 95% by weight) and surfactant (from 0 to 20% by weight).

7. A process for treating plants against phytopathogenic fungi, which consists in applying to these plants an effective quantity of a compound according to one of claims 1 to 3.

* * * * *